United States Patent [19]

Rydell

[11] Patent Number: 4,547,193
[45] Date of Patent: Oct. 15, 1985

[54] CATHETER HAVING EMBEDDED MULTI-APERTURED FILM

[75] Inventor: Mark A. Rydell, Excelsior, Minn.

[73] Assignee: Angiomedics Incorporated, Plymouth, Minn.

[21] Appl. No.: 596,920

[22] Filed: Apr. 5, 1984

[51] Int. Cl.⁴ .............................................. A61M 25/00
[52] U.S. Cl. .................................... 604/282; 128/658; 138/127
[58] Field of Search .................... 604/282, 280, 95; 128/656–658; 138/127, 124, 137–139; 428/172, 174, 36

[56] References Cited

U.S. PATENT DOCUMENTS 3,416,531 12/1968 Edwards ................................ 604/95
3,924,632 12/1975 Cook .................................... 604/282
4,425,919 1/1984 Alston, Jr. et al. ............. 604/282 X Primary Examiner—Stephen C. Pellegrino
Attorney, Agent, or Firm—Orrin M. Haugen; Thomas J. Nikolai

[57] ABSTRACT

A tubular angiographic catheter containing a wrapped multi-apertured film embedded in the walls thereof. The film material and aperture size, shape and pattern may be varied to produce a tailored torque transfer characteristic for enhancing the maneuverability of the distal end of the catheter by manipulating its proximal end.

7 Claims, 5 Drawing Figures

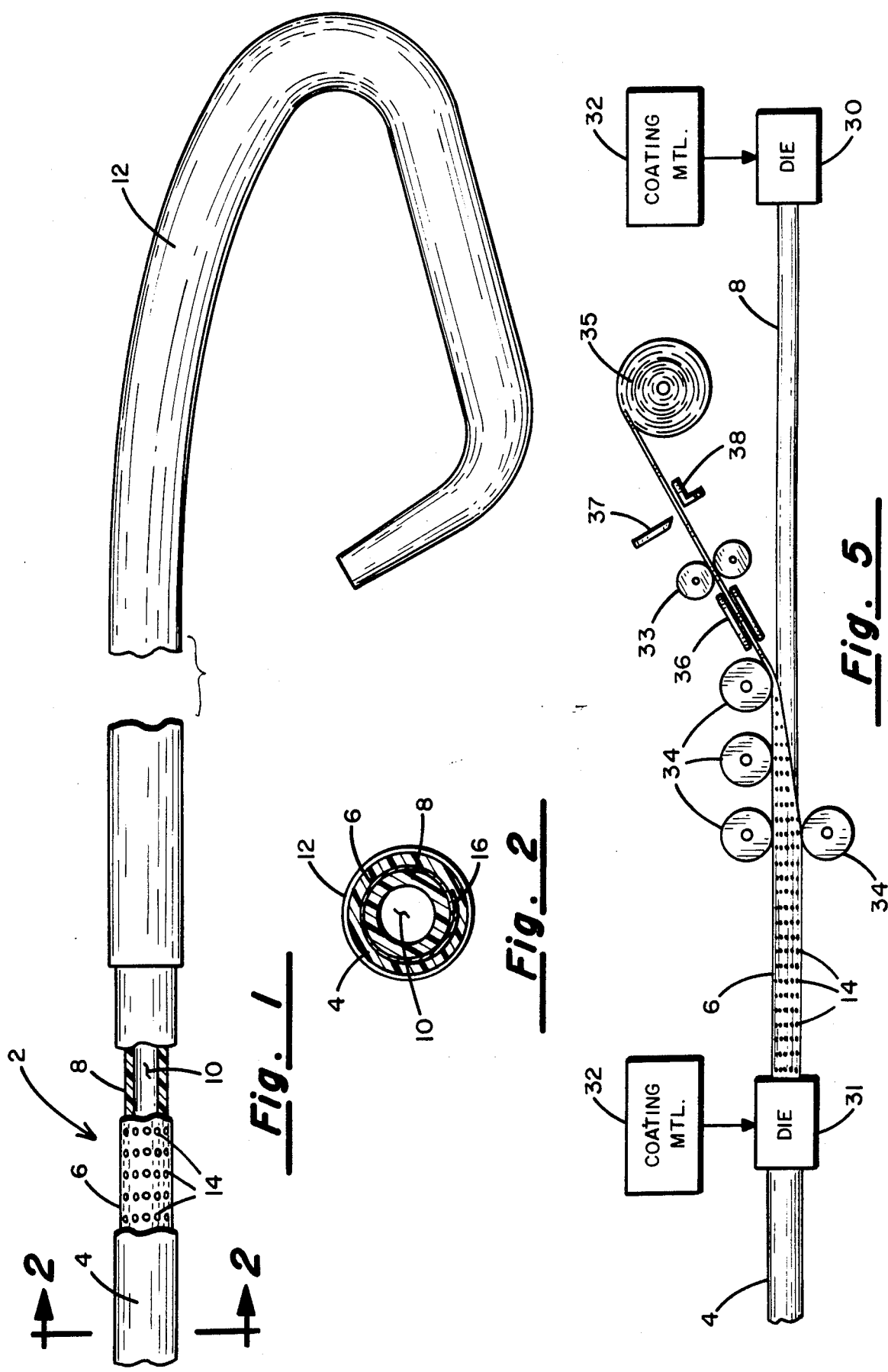

CATHETER HAVING EMBEDDED MULTI-APERTURED FILM

BACKGROUND OF THE INVENTION

The present invention relates to catheters and in particular to an angiographic cathether having a tubular-wrapped apertured film embedded between inner and outer layers and surrounding a centrally disposed lumen.

Intravascular catheters have long been used in various medical procedures for facilitating patient treatment. For example, cardiac pacemaker leads having stimulating and sensing electrodes are commonly routed through the vascular system into the heart. In other treatment modalities, medicants and/or radiopaque dyes are injected through the catheters after they have been routed through the vascular system and brought to bear at a desired treatment site. Thereafter, for a variety of treatment modalities, a radiopaque dye may be injected through a lumen in the catheter, whereby the dye containing body organs can be fluoroscopically inspected.

Such catheters find particular use in procedures dealing with the treatment of heart diseases, arteriosclerosis or the like. A problem attendant with the use thereof, however, occurs in maneuvering the catheter along a desired veinous route which may require the twisting and turning of the catheter. While a stylet may be inserted into a lumen in the catheter to make the otherwise limp catheter more rigid or to cause it to conform to the stylet shape, for many procedures a stylet is not easily accomodated or may cause the catheter to become too rigid and, in other cases it does not readily facilitate torsional movements of the catheter. Accordingly, a need exists for catheters having desirable torque transfer characteristics.

U.S. Pat. No. 3,485,234 describes a catheter construction in which a stainless steel braid is embedded in the wall of the tubular catheter to add desirable torque transfer characteristics to the catheter and thereby improve the maneuverablity of a thermoplastic tip attached thereto. This latter catheter, however, suffers in that the related fabrication process (disclosed in U.S. Pat. No. 3,485,704) is somewhat slow and does not readily facilitate the fabrication of catheters with tailored torque transfer characteristics.

The present invention, on the other hand, contemplates the incorporation of a multi-apertured film material into the core of a catheter so as to improve its torsional maneuverability and to facilitate its fabrication. Because the film may be formed using various types, sizes and shapes of apertures along its length and/or different types of film materials, such a catheter can be tailored to have torque transfer characteristics meeting different specific applications.

In accordance with the present invention, the catheter is formed by extruding a hollow tubular center core and about the periphery of which core the apertured film is wrapped. Thereafter, the wrapped core is subjected to a second extrusion operation during which an outer layer is deposited over the wrapped core so as to form the composite catheter body. A thermoplastic tip may then be attached and formed to a desired shape. Alternatively, because the method of the present invention allows the intermittent applications of film along the catheter length, it is not a requirement that a separate distal tip member be bonded to the catheter body to achieve desired tip characteristics. One or more lumens may also be formed in the catheter for accomodating a stylet and/or the injection of radiopaque dyes or pressure measurement. The same type of approach can be applied by those skilled in the art to a variety of catheters, including pacing leads, physiologic sensors and the like.

SUMMARY OF THE INVENTION

An intravascular catheter containing a wrapped film layer having a plurality of apertures formed therein, which film is co-extensive with the catheter so as to transfer operator induced torsional movement at its proximal end to manipulate the distal end of the catheter in a desired fashion. The catheter in cross-section comprises an outer layer surrounding the multi-apertured film, the film surrounding an inner tubular layer and having a centrally disposed lumen. The film may be fabricated from any number of suitable metallic or plastic materials of a thickness dictated by the geometric constraints in which the catheter is to be used and the apertures may be formed in any number of geometric shapes, spacings and/or arrangement along said catheter so as to tailor the flexibility and torque transfer characteristics thereof.

The catheter may be fabricated by initially extruding a hollow tubular inner core about which pre-formed multi-apertured film is wrapped. The wrapped inner layer is next extruded through a second dye whereat an outer layer of a biocompatible material, which may or may not be identical to the material of the inner layer, is deposited thereover so as to form the catheter body stock. Thereafter, the body stock is cut to length and a formed thermoplastic tip is attached to the distal end. Because of the manner in which the apertured film can be tailored, it is also possible to create a distal tip portion integrally with the catheter body, thereby obviating the need to bond or weld the tip to the body.

The details of the construction and the objects, advantages and distinctions of the present improved catheter will become more apparent upon reference to the following description thereof with respect to the following drawings. Before referring thereto, though, it is to be recognized that the description is made only with respect to the presently preferred embodiment and some presently contemplated modifications. Accordingly, still other modifications may occur to those skilled in the art without departing from the spirit and scope thereof.

DESCRIPTION OF THE DRAWINGS

FIG. 1 shows a partially sectioned and layered elevation view of an angiographic catheter employing a wrapped, multi-apertured film core;

FIG. 2 shows a cross-section view along lines 2—2 of FIG. 1;

FIG. 5 shows a block diagram of the process for fabricating the present improved catheters.

DESCRIPTION OF THE PREFERRED EMBODIMENT

Figure 4:
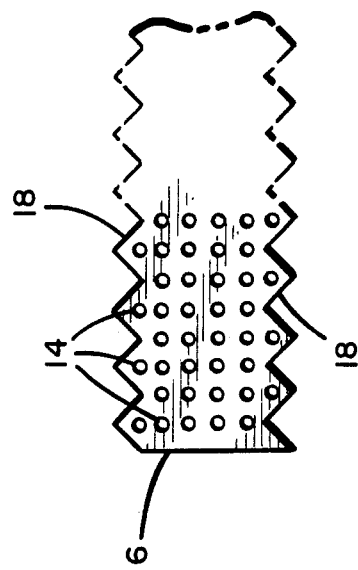
FIG. 4 shows a section of multi-apertured film, the sides of which will butt to one another when wrapped about the inner core.
Figure 3:
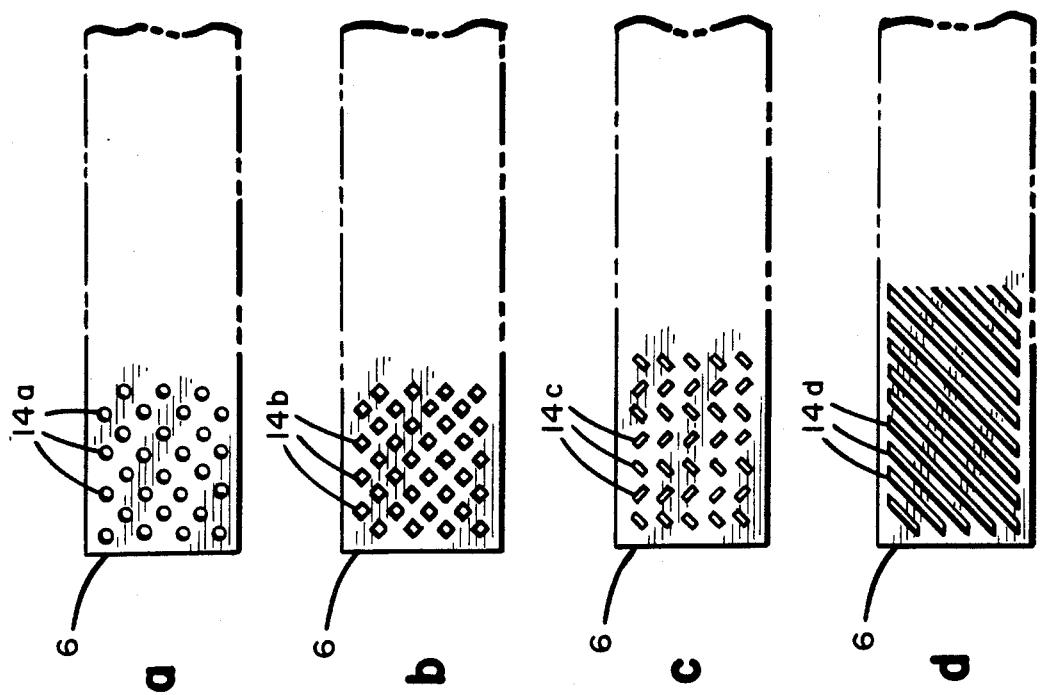
FIG. 3 shows a number of alternative aperture designs which may be formed in the film to impart different torque transfer characteristics to the catheter.

Referring first to FIGS. 1 and 2, respectively shown are a side elevation and a cross-sectional view of an improved intravascular catheter containing a wrapped, multi-apertured film. In particular, the catheter 2 of FIG. 1 is partially broken away so as to show its different internal layers and the cross-sectional view of FIG. 2 reveals other constructional features. As can be seen, the catheter body comprises an outer layer 4 overlying a film member 6 which may be either concentrically or spirally wrapped about a lower lying inner tubular member 8 having a centrally disposed lumen 10. In one arrangement, attached to the distal end of the catheter 2 is a formed thermoplastic tip member 12 which may be torsionally manipulated by twisting the catheter 2 at its proximal end as it is inserted through a vein or artery. The torsional movement is transferred by the film containing body of the catheter to the tip 12.

The inner and outer tubular layers 8 and 4 of the catheter 2 may be fabricated from any number of biocompatible materials, for example, polyurethane, polyethylene or Teflon. The specific material selected for any catheter, however, is dependent upon its end-use or application, its desired flexibility and its size.

Wrapped about the extruded hollow tube-like inner layer 8 is the multi-apertured film 6 which, too, may be fabricated from any number of different types and thicknesses of materials, such as, for example, metal foils, Mylar film or Kapton film. Prior to being embedded in the catheter body, a plurality of apertures 14 are formed through the film 6 in a desired pattern specifically designed to give a desired torque characteristic to the resulting catheter. While FIG. 1 shows the apertures 14 as being formed as round holes, it is to be recognized that any number of other geometric shapes may be employed. Further the spacings and patterns between the various apertures 14 are controllable. It should also be recognized that the aperture shape and/or pattern and/or film thickness may be varied in different regions along the length of the catheter 2 so as to tailor the flexibility of the catheter 2 in these regions.

Depending upon the type and thickness of the film 6, the apertures 14 may be formed via any number of methods. As presently contemplated, these methods would include chemical etching, laser burning and punching or stamping, such as employed in various expanded metal fabrication techniques. In any case, though, apertures 14 of desired sizes, geometric shapes and spacings are let through the film 6 so as to produce a desired torque transfer characteristic when embedded in the body of the catheter 2. Thus, depending upon the resultant flexibility of the film 6, operator induced torque is transferred differently, with greater or lesser amounts of movement at the tip 12.

As regards the catheter's torque transfer characteristics, attention is next directed to FIGS. 3(a) through 3(d) wherein a number of alternatively shaped and patterned apertures 14 are shown and which, for a film 6 of an identical thickness, produce differing amounts of torque transfer. Specifically, the film of FIG. 3(a) contains a plurality of round apertures 14a; whereas, the film of FIG. 3(b) contains a plurality of square apertures 14b. The film of FIG. 3(c), on the other hand, contains a plurality of orthogonal and offset rectangular apertures 14c while the film of FIG. 3(d) contains a plurality of diagonally formed slits 14d. Of the films of FIGS. 3(a) through 3(d), films (c) and (d) tend to be more flexible than either FIGS. 3(a) or 3(b) and, accordingly, do not transfer torque as well. However, films of FIGS. 3(c) and 3(d) permit a greater amount of bending of the catheter 2 than do the films of FIGS. 3(a) and 3(b). Accordingly, it is to be recognized that the film 6 may be selectively patterned in different regions along its length with apertures 14 of different geometric shapes so as to yield a catheter 2 with a tailored torque transfer characteristic. These characteristics may be further varied by forming the film 6 with a varying thickness over its length, although as presently contemplated a film 6 of a uniform thickness in the range of 0.5 mils to 3 mils is preferred. It should be readily apparent though that the film 6 is much more amenable to the fabrication of torque-tailored catheters 2 than is the braided wire previously used.

Attendant with the use of a multi-apertured film 6, as the primary torque-transfer medium are concerns as to whether or not the torque transfer characteristic or the catheter's cross-sectional diameter may be affected by overlapping the wrapped side edges of the film 6 as at 16 in FIG. 2. If there is such a concern, a butt seam 16 may alternatively be employed. In that regard, in lieu of a longitudinal and parallel butt seam 16, it may be preferable to employ an interlocking butt seam, which will result when the film shown in FIG. 4 is wrapped about a cylindrical substrate. Here, the opposite side edges 18 of the film 6 are cut in a saw-tooth fashion so that the teeth of one side interlock with the teeth of the other side, when wrapped around the inner core 8. It is to be recognized, however, that while such a configuration may enhance the uniformity of the torque transfer characteristics along the length of the catheter 2, it does so at the potential of increased fabrication complexity. Futhermore, for most applications, such as angiographic applications, this complexity may not be needed, since sufficient tensile strength is achieved, via an overlapped seam 16 in the fashion of FIG. 2.

As mentioned, the catheter 2 of FIGS. 1 and 2 contains a centrally disposed lumen 10 through which medication and/or radiopaque dyes may be injected into desired body areas. While a single lumen 10 is shown, additional lumens may also be formed in the catheter 2 in accordance with known techniques and for a variety of purposes.

Redirecting attention to FIG. 1, it it to be recalled that the tip 12 is formed from a thermoplastic, thermosetting material. Specifically, a hollow tubular length of this material may be inserted over and secured to the distal end of the catheter 2. Different types of thermosetting materials may then be used to secure the tip 12 to the catheter body. These tip materials, upon the application of heat, are also easily bent and/or twisted into a desired tip shape configuration and which may be retained following a quenching step. Thereafter, during a medical procedure, the formed tip 12 is more readily torsionally maneuvered because of the inclusion of the multi-apertured film 6.

Directing attention now to FIG. 5, a general block diagram is shown of the manner of fabrication of the catheter 2. Specifically, the catheter 2 is fabricated to a desired size between 3 and 9 French by first extruding the inner tubular layer 8 through a die 30, which die 30 is injection fed with a plastic material from a supply resevoir 32. The inner tubular layer 8, upon cooling, is next passed through a forming station where a plurality of sequential rollers 34 lay the apertured film 6 onto the surface of the inner tubular layer 8 and successively wrap the film 6 thereabout as the inner tubular layer 8 passes therealong. Thus, as the film 6 leaves the last roller 34, it has been concentrically wrapped about the inner extruded tubular member 8, either with or without overlap at the side edges. This invention also contemplates that the type of machine used to spirally wrap a layer of paper or metal ribbon in forming coaxial electrical cable can be used to spirally wrap the apertured film 6 about the central core 8. Next, the wrapped inner layer 8 is passed through a second extrusion die 31 that, too, is fed with the same or a different plastic material as in the supply reservoir 32 so as to deposit the outer layer 4 over the film 6. The material comprising the outer layer, in turn, flows through the apertures 14 and bonds to the inner layer 8 so as to form an integral structure.

During the fabrication process, the film 6 is not necessarily continuously applied to the inner layer 8, but rather may be intermittently applied in predetermined lengths so as to leave a space between each section of film 6 that is deposited along the inner layer 8. In order to achieve this end, the film 6 is fed as a continuous flat strip by pinch rollers 33 and 36 from a supply roll 35 past a blade 37 cooperating with an anvil 38 that is used to cut the film at desired lengths when actuated by means (not shown). Thus a continuous length of catheter body stock is produced which may subsequently be cut in the region of the space between the sections of film 6 to form individual catheter bodies.

While the present invention has been described with respect to its presently preferred embodiment and the method of making same, it is to be recognized that still other modifications may be made thereto without departing from the spirit and scope hereof. Accordingly, it is contemplated that the following claims shall be interpreted so as to include all equivalent embodiments within the spirit and scope thereof.

What is claimed is:

1. An improved intravascular catheter comprising a flexible, plastic tubular member having at least one lumen, a thin film member having a plurality of apertures formed therethrough and said film being embedded in said plastic and wrapped about said central lumen with its longitudinal edges butted to one another for imparting predetermined torsional rigidity to said tubular member.

2. A catheter as set forth in claim 1 wherein the longitudinal edges are formed to interlock with one another.

3. A catheter as set forth in claim 1 wherein said plurality of apertures comprises a plurality of parallel slits.

4. A catheter as set forth in claim 1 wherein said film includes a plurality of zones displaced from one another, the geometric shape and density of the apertures in each of said zones being established to impart a predetermined flexibility and torque transfer characteristic to each of said zones, depending upon desired characteristics of said catheter.

5. A catheter as set forth in claim 1 wherein said film is an extruded thermoplastic material.

6. A catheter as set forth in claim 1 wherein said film is a metallic film sheet.

7. A catheter as set forth in claim 1 and further including a thermoplastic tip having a bore therethrough in communication with said lumen and attached to a distal end of said catheter.

* * * * *